United States Patent [19]

Nunn et al.

[11] 4,182,768

[45] Jan. 8, 1980

[54] PROPHYLAXIS OR TREATMENT OF THROMBOSES AND INHIBITION OF PLATELET AGGREGATION IN HUMAN BLOOD

[75] Inventors: Barbara Nunn, Sutton; Keith H. Baggaley, Redhill, both of England

[73] Assignee: Beecham Group Limited, England

[21] Appl. No.: 910,292

[22] Filed: May 30, 1978

[30] Foreign Application Priority Data

May 31, 1977 [GB] United Kingdom ............... 22903/77

[51] Int. Cl.² .................. A61K 31/425; A61K 31/445
[52] U.S. Cl. ...................................... 424/267; 424/270
[58] Field of Search ............................... 424/267, 270

[56] References Cited

U.S. PATENT DOCUMENTS 3,227,715  1/1966  Buo ....................................... 424/250

*Primary Examiner*—Stanley J. Friedman
*Attorney, Agent, or Firm*—Jacobs & Jacobs

[57] ABSTRACT

A method for the prophylaxis or treatment of thromboses in humans which comprises administering to a human in need thereof a therapeutically effective amount of a compound of the formula (II)

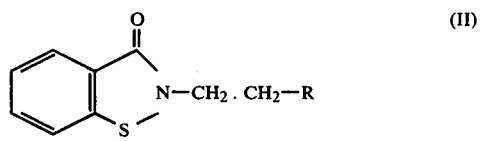

(II)

or a pharmaceutically acceptable acid addition salt thereof, wherein R is 1-piperidyl or 1-pyrrolidyl. Compounds of the formula (II) are also useful for the inhibition of platelet aggregation in vitro or in vivo.

17 Claims, No Drawings

PROPHYLAXIS OR TREATMENT OF THROMBOSES AND INHIBITION OF PLATELET AGGREGATION IN HUMAN BLOOD

This invention relates to antithrombotic compositions and in particular to compositions comprising as active ingredient one or more compounds selected from a small class of benzisothiazolones.

Arterial thrombosis develops initially from the aggregation of blood platelets within the artery. This aggregate may eventually lead to the formation of fibrin and the formation of a consolidated occlusive thrombus. The most widely used therapy for thrombosis is the use of anti-coagulant agents, which influence blood clotting, However, although effective in venous thrombosis, where the thrombus is formed mainly of fibrin, anti-coagulant therapy has no effect on platelet aggregation and has therefore limited effectiveness in arterial thrombosis. It is now accepted that anti-coagulant drugs have little to offer in the treatment of arterial thrombosis.

With the increasing recognition of the primary role of platelets in thrombosis, attention had turned to drugs which are capable of inhibiting the aggregation of platelets.

U.S. Pat. Specification No. 3,227,715 discloses a class of benzisothiazolones of the formula (I):

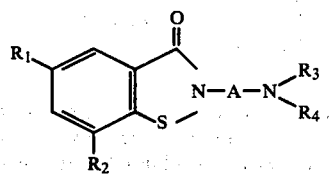

wherein A represents a lower alkylene of 2 to 4 carbon atoms, $R_1$ and $R_2$ are hydrogen or halogen, $R_3$ and $R_4$ represent hydrogen, lower alkyl, cycloalkyl, hydroxyalkyl of 2 to 4 carbon atoms or alkoxyalkyl of 2 to 4 carbon atoms, and $R_3$ and $R_4$ together with the nitrogen atom on which they are substituted stand for an unsubstituted or lower alkyl substituted heterocyclic ring having from 5 to 6 atoms in the ring; as being useful for the therapy of inflammatory processes.

It has now been found that two of the benzisothiazolones disclosed in that patent have exceptional activity as inhibitors of platelet aggregation and are therefore useful for the prophylaxis and treatment of thrombosis.

U.S. Pat. No. 3,227,715 does not suggest any antithrombotic activity for any of the compounds described therein.

Accordingly, the present invention provides a process for inhibiting platelet aggregation which comprises the addition to human blood in vitro or in vivo of a compound of formula (II), or a pharmaceutically acceptable acid addition salt thereof:

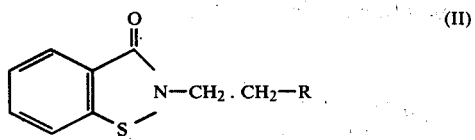

wherein R is 1-piperidyl or 1-pyrrolidyl.

Suitable acid addition salts include inorganic salts such as sulphates, nitrate, phosphate, and borate, hydrohalides e.g., hydrochloride, hydrobromide, and hydroiodide, and organic acid addition salts such as acetate, oxalate, tartrate, maleate, citrate, succinate, benzoate, ascorbate, methanesulphonate, and p-toluenesulphonate.

Preferred salts are the hydrochloride and hydrobromide.

For in vivo applications this invention therefore provides a method of prophylaxis or treatment of thrombosis in humans which comprises administration to humans of a compound of formula (II) or a pharmaceutically acceptable acid addition salt thereof.

The compounds are generally administered to the patient in the form of a composition formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrollidone; fillers, for example lactose, sugar, maize-starch, calcium phosphate, sorbitol, or glycine; tabletting lubricants for example magnesium stearate, talc, polyethylene glycol, or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate or acacia; non-aqueous vehicles (which may include edible oils) for example almond oil, fractionated coconut oil, oily esters, such as glycerine, propylene glycol, or ethyl alcohol; preservatives for example methyl or propyl p-hydroxybenzoate, or sorbic acid, and if desired conventional flavouring or colouring agents. The compound may also if desired be incorporated in a foodstuff, for example in the form of a biscuit.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into suitable vials or ampoules and sealing. Advantageously, adjuvants such as local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight preferably from 10-60% by weight, of the active material, depending on the method of administration. Where the compositions comprise dosage units, each unit will preferably contain from 1–500 mg, of the active ingredients.

The dosage employed for adult treatment will of course depend on the dose response characteristics of the particular active ingredient, and also on the blood volume and condition of the patient, but will normally be in the range of 0.01 to 30 mg/kg/day depending on the route and frequency of administration. The preferred dose is 10 to 500 mg, orally 1 to 3 times a day for an adult human. The method of the invention is useful to prevent clot formation for example after surgery to prevent postoperative thrombosis; in geriatric patients to prevent transient cerebral ischemic attacks; and long-term prophylaxis following myocardial infarcts and strokes.

The in vitro aspect of this invention comprises the addition of a compound (II) or a pharmaceutically acceptable salt thereof to whole blood or platelet rich concentrates and has applications in the storage of whole blood in blood banks, and whole blood to be used in heart-lung machines, or to be circulated through organs, e.g. heart and kidneys, which have been removed from a cadaver and prior to transplant.

The dosage for such an addition is preferably from 0.01 to 5 micrograms/ml of whole blood.

The compounds of formula (II) may be prepared as described in U.S. Pat. No. 3,227,715.

Biological Data

Two compounds of formula (II) were tested for their ability to inhibit platelet aggregation in the guinea pig ex vivo as follows:

METHOD

Male guinea pig weighing 250-300 g were orally dosed 1% methyl cellulose (5 ml/kg) in which the compound under test was suspended. Control animals were given methyl cellulose alone. Two hours later, each animal was killed and 4.5 ml blood drawn from the inferior vena cava into 0.5 ml trisodium citrate dihydrate. Platelet-rich-plasma (PRP) was prepared from each blood sample by centrifugation at 450 g for 5 min. The platelet concentration in each sample of PRP was adjusted with autologous platelet-poor-plasma measured turbidometrically (G.V.R. Born, 1962, Nature, 194, 927-929) at 37° using a Bryston aggregometer coupled to a pen-recorder. The concentration of collagen producing approximately 50% maximal aggregation and the concentration of ADP producing first-phase aggregation were compared in PRP samples from control and drug treated animals. Results are summarised in Table 1 together with some known anti-aggregant compounds for comparison.

In Table 1 the dose ratio represents the ratio of the concentration of aggregating agent to cause aggregation in PRP from drug-treated animals to the concentration of aggregating agent to cause aggregation in PRP from control animals.

The results are shown in Table 1.

TABLE 1

| Compound tested | Dose, P.O. (mmol/kg) | Dose Ratio Collagen | ADP |
|---|---|---|---|
| 2-[β-(1-piperidyl)-ethyl]-1,2,-benz-isothiazol-3-one | 0.15 | >18.2* | 8.3* |
|  | 0.08 | 6.7* | 1.4* |
| 2-[β-(1-pyrrolidinyl)-ethyl]-1,2-benz-isothiazol-3-one | 0.15 | 13.9* | 1.9 |
|  | 0.08 | { 6.6* <br> 7.5* | { 1.3 <br> 1.5* |
| Sulfinpyrazone | 0.3 | 2.1* | 1.2 |
| Aspirin | 0.15 | 2.2* | 1.3 |
| 4-(4-morpholinyl)-2-(1-piperazinyl)-thieno [3,2-d]pyrimidine dihydrochloride. | 0.15 | 3.0* | 1.3 |

We claim:
1. A method of treating thromboses in humans which comprises administering to a human in need thereof a therapeutically effective amount of a compound of the formula (II):

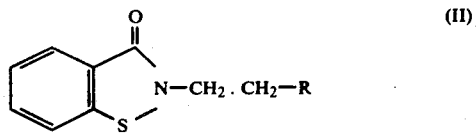

or a pharmaceutically acceptable acid addition salt thereof wherein R is 1-piperidyl or 1-pyrrolidyl.

2. A method according to claim 1 wherein the compound is in the form of the hydrochloride or hydrobromide salt.

3. A method according to claim 1 wherein the administration is oral.

4. A method according to claim 1 wherein the dose is from 10 to 500 mg per day.

5. A method according to claim 1 wherein the dosage is from 0.01 to 30 mg/kg per day.

6. A method according to claim 1 wherein the compound is administered in the form of a pharmaceutically acceptable acid addition salt selected from the group consisting of a sulphate, nitrate, phosphate, borate, hydrochloride, hydrobromide, hydroiodide, acetate, oxalate, tartrate, maleate, citrate, succinate, benzoate, ascorbate, methanesulphonate and p-toluenesulphonate.

7. A method according to claim 2 in oral administration form.

8. A method according to claim 1 in parenteral administration form.

9. A method of inhibiting platelet aggregation in whole blood or platelet rich concentrates which comprises adding to said whole blood or platelet rich concentrates, from 0.01 to 5 mg/ml of whole blood, of a compound of the formula (II):

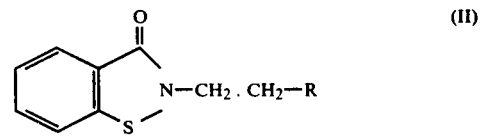

or a pharmaceutically acceptable acid addition salt thereof, wherein R is 1-piperidyl or 1-pyrrolidyl.

10. A method according to claim 9 wherein the compound is in the form of the hydrochloride or hydrobromide salt.

11. A method according to claim 9 wherein the compound is added in the form of a pharmaceutically acceptable acid addition salt selected from the group consisting of a sulphate, nitrate, phosphate, borate, hydrochloride, hydrobromide, hydroiodide, acetate, oxalate, tartrate, maleate, citrate, succinate, benzoate, ascorbate, methanesulphonate and p-toluenesulphonate.

12. A method of inhibiting platelet aggregation in the human blood which comprises administering to a human in need thereof a platelet aggregation inhibiting amount of a compound of the formula (II):

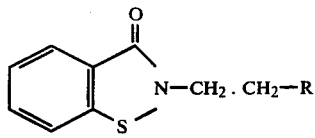

or a pharmaceutically acceptable acid addition salt thereof, wherein R is 1-piperidyl or 1-pyrrolidyl.

13. A method according to claim 12 wherein the compound is in the form of the hydrochloride or hydrobromide salt.

14. A method according to claim 12 wherein the administration is oral.

15. A method according to claim 12 wherein the compound is administered in the form of a pharmaceutically acceptable acid addition salt selected from the group consisting of a sulphate, nitrate, phosphate, borate, hydrochloride, hydrobromide, hydroiodide, acetate, oxalate, tartrate, maleate, citrate, succinate, benzoate, ascorbate, methanesulphonate and p-tolunesulphonate.

16. A method according to claim 13 in oral administration form.

17. A method according to claim 12 in parenteral administration form.

* * * * *